US006376516B1

(12) United States Patent
Joshi et al.

(10) Patent No.: US 6,376,516 B1
(45) Date of Patent: Apr. 23, 2002

(54) NOSCAPINE AND NOSCAPINE DERIVATIVES, USEFUL AS ANTICANCER AGENTS

(75) Inventors: Harish C. Joshi, Decatur, GA (US); Ye Keqiang, Baltimore, MD (US); Judith Kapp, Atlanta, GA (US); Fuqiang Liu, Piscataway, NJ (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/582,375

(22) PCT Filed: Jul. 20, 1998

(86) PCT No.: PCT/US98/14979

§ 371 Date: Sep. 26, 2000

§ 102(e) Date: Sep. 26, 2000

(87) PCT Pub. No.: WO99/08528

PCT Pub. Date: Feb. 25, 1999

Related U.S. Application Data
(60) Provisional application No. 60/057,037, filed on Aug. 19, 1997.

(51) Int. Cl.⁷ ............................................. A61K 31/445

(52) U.S. Cl. ........................................ 514/320; 514/319

(58) Field of Search ................................. 514/319, 320

(56) References Cited

U.S. PATENT DOCUMENTS

| 3,108,106 A | 10/1963 | Maillard | 260/285 |
|---|---|---|---|
| 4,816,462 A | 3/1989 | Nowicky | 574/279 |
| 4,994,281 A | 2/1991 | Muranishi et al. | 424/497 |
| 5,100,669 A | 3/1992 | Hyon et al. | 424/426 |
| 5,213,808 A | 5/1993 | Bar-Shalom et al. | 424/473 |

FOREIGN PATENT DOCUMENTS

| CA | 1191837 | 8/1985 |
|---|---|---|
| JP | 53-41415 | 4/1978 |
| JP | 3-42279 | 6/1991 |
| JP | 63-183540 | 6/1991 |
| WO | WO 83/00486 | 2/1983 |

OTHER PUBLICATIONS

Al–Yuhya et al., "Noscapine", Analytical Profiles of Drug Substances, vol. 11 Academic Press, pp. 407–461, 1982.*
Battersby, et al., "Concerning the Biosynthesis of Narcotine", Tetrahedron Lett. 11:669–673, 1965.*
Al–Yuhya and Hassan, in K.Florey (Ed.), "Noscapine," Analytical Profiles of Drug Substances, vol. 11 Academic Press, pp. 407–461 (1982).
Battersby, et al., "Concerning The Biosynthesis of Narcotine," Tetrahedron Lett. 11:669–673 (1965).
Empey, D.W., et al., Eur. J. Clin. Pharmacol. 16, 393–397 (1979).
Fleishchhacker, et al., Chem. Monthly 120:765–769 (1989).
Gavrieli, Y. et al., "Identification of Programmed Cell Death in Situ via Specific Labeling of Nuclear DNA Fragmentation," J. Cell. Bio. 119:493–501 (1992).
Gorczyca, W. et al., "Detection of DNA Strand Breaks in Individual Apoptotic Cells by the in Situ Terminal Deoxynucleotidyl Transferase and Nick Translation Assays,"Cancer Res. 53:1945–1951 (1993).
Joshi, et al., "y–Tubulin is a centrosomal protein required for cell cycle–dependent microtybule nucleation," Nature, 356:80–83 (1992).
Kerekes and Bognar, "Synthese des Gnoscopins (DL–Narcotin)," J. Prakt. Chem. 313:923–928 (1971).
Molnar, et al., "In vitro antiproliferative effects of tricyclic psychopharmaceutical agents and synergism with some resistance modifiers," Anticancer Res., 12(1):273–280 (1992).
Moore, M.W., et al., "Introduction of Soluble Protein into the Class I Pathway of Antigen Processing and Presentation," Cell 54:777–785 (1988).
Perkin and Robinson, "Synthesis and Resolution of Gnoscopine," J. Chem. Soc. [London], 99:775–798 (1911).
Peyrot, V. et al., "Mechanism of Binding of the New Antimitotic Drug MDL 27048 to the Colchicine Site of Tubulin: Equilibrium Studies," Biochemistry 31:11125–11132 (1992).
Pinko,C., "Single–chain Recombinant Human Cytomegalovirus Protease," J. Biol. Chem., 270(40):23634–23640 (1995).
Powers, J.C., et al., "Reaction of Porcine Pancreatic Elastase with 7–Substituted 3–Alkoxy–4–chloroisocoumarins: Design of Potent Inhibitors Using the Crystal Structure of the Complex Formed with 4–Chloro–3–ethoxy–7–guanidinoisocoumarin," Biochemistry 29:3108–3118 (1990).

(List continued on next page.)

*Primary Examiner*—Dwayne C. Jones
(74) *Attorney, Agent, or Firm*—Bruce D. Gray; Kristin D. Mallatt; Kilpatrick Stockton LLP

(57) ABSTRACT

Compounds such as formula (I) are useful in the treatment of tumor cells and the treatment of cancer.

(I)

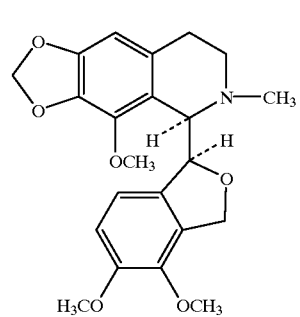

6 Claims, No Drawings

OTHER PUBLICATIONS

Prior, S.; "Borane adducts of narcotine, hydrastine and their reduction products," *Arch. Pharm.* 316(9):737–746 (1983) (chemical Abstracts vol. 99, 176115z (1983).

Sam, J. et al., "Preparation and Properties of Some Relatives of Noscapine," *J. Pharm. Sci.* 57:–1755–1759 (1968).

Shono, T. et al., "New Electroreductive Synthesis of Phthalide Alkaloids," *Tetrahedron Lett.*, 21:1351–1354 (1980).

Walton, M.I. et. al., "Constitutive Expression of Human Bcl–2 Modulates Nitrogen Mustard and Camptothecin Induced Apoptosis," *Cancer. Res.* 53:1853–1861 (1993).

"Noscapine," Chemical Abstracts, p. 1063 No. 6638, 1987.

* cited by examiner

NOSCAPINE AND NOSCAPINE DERIVATIVES, USEFUL AS ANTICANCER AGENTS

This application claims benefit to U.S. Provisional Application Serial No. 60/057,037 filed on Aug. 19, 1997, the entire contents of which is hereby incorporated by reference.

The subject matter of the present invention was developed in part by one or more grants of the United States Government, GM51389 and CA70372.

BACKGROUND OF THE INVENTION

Two important events in the cell division cycle are the duplication of the chromosomal DNA and the separation of the duplicated chromosomes. These events occur in two discrete phases: the synthetic phase (S-phase) and the mitotic phase (M-phase), which are separated from each other by distinct gaps in time, gap 1 (G1) and gap 2 (G2). The proper coordination of these events is achieved by checkpoint pathways that delay the progression of the cell cycle when proper completion of one phase is disrupted by physical damage or other means. Under normal circumstances, if the extent of damage is irreparable, most cells initiate a sequence of biochemical events leading to programmed cell death or apoptosis. Deregulation in any one or more of these checkpoint mechanisms sometimes leads to genetic instability which is a primary step for a tumor to evolve into invasive malignant state. The chemotherapeutic management of various cancers is achieved by drugs that block either the S-phase, the M-phase, or that block regulatory or metabolic pathways impinging upon the cell cycle machinery. For example, some drugs affect the functions or structures of DNA or RNA, others interfere with enzymes involved in folate, purine, or pyrimidine metabolism, or the function of mitotic spindles. Anti-mitotic drugs such as vinica akaloids and taxoids can arrest cells in M-phase by interacting with mitotic spindle components, microtubules. Microtubules are one of the major filamentous components of the cytoskeleton, and, together with actin and intermediate filaments, they organize the cellular cytoplasm. In interphase cells a dynamic radial array of microtubules emanates from the centrosome at the cell center. In this array, the fast growing and fast shrinking plus ends of microtubules project distally from the center. During mitosis, the duplicated centrosomes nucleate assembly of much more dynamic and more numerous polymers as they move apart to form the opposite poles of the mitotic spindle. The increased dynamics and number of microtubules enhance the chance-encounter of growing microtubules with the primary construction of the duplicated chromatid pairs. Upon attaching to microtubules, chromosomes undergo a series of movements eventually leading to their conversion and final assembly at the mid-plate during metaphase. The onset of the next event in mitosis, the anaphase, is delayed until each of the chromatid pairs is assembled at the metaphase mid-plate and proper tension is generated on the attached sister chromatids.

Dynamic assembly or disassembly of microtubules is required for the morphogenesis of mitotic spindle. Accordingly, small organic molecules that modulate the dynamics of microtubules primarily because some of the microtubule interacting agents are useful for chemotherapeutic management of certain kinds of tumors. There are two classes of these anti-microtubule agents: those that prevent the assembly of tubulin, and those that promote the assembly of tubulin. A prototypic example of a potent assembly inhibitor is colchicine. Others are analogs of colchicine such as podophyllotoxin, MTC [(2-methoxy-5-(2,3,4-trimethoxyphenyl)-2,4,6-cycloheptatrien-1-one)], TCB (2,3,4-trimethoxy-4'-carbomethoxy-1,1'-biphenyl) and TKB (2,3,4-trimethoxy-4'-acetyl-1,1'-biphenyl), and vinica akaloids. Taxol and its analogs represent a class of compounds that promote the assembly of microtubules. It is now clear that although all of these microtubule drugs prevent cell division, only a select few have been useful clinically. In addition, there are differences regarding the toxicity and the efficacy of these drugs for distinct classes of tumors.

Applicants have discovered that the antitussive noscapine and its derivatives are useful in the treatment of neoplastic diseases. Noscapine is used as an antitussive drug and has low toxicity in humans. Noscapine arrests mammalian cells at mitosis, causes apoptosis in cycling cells, and has potent antitumor activity. Noscapine is an alkaloid from opium, and is readily available as a commercial byproduct in the commercial production of prescription opiates. Applicants have unexpectedly discovered that noscapine promotes assembly of tubulin subunits.

BRIEF DESCRIPTION OF THE INVENTION

Applicants have synthesized derivatives of noscapine, a known antitussive having low toxicity in humans, and have shown they promote assembly of tubulin subunits, a characteristic suitable for the treatment of tumours and various neoplastic diseases.

DETAILED DESCRIPTION OF THE INVENTION

The present invention relates to a pharmaceutical composition comprising a compound of the formula

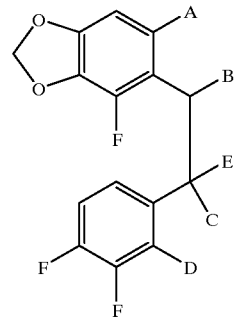

wherein: A is (i)

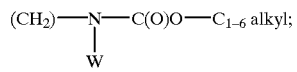

and W is $C_{1-6}$ alkyl;

(ii)

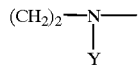

and forms a six membered ring with B, said ring containing one nitrogen;

Y is
  (a) $C_{1-6}$ alkyl, or H;
  (b) $C(O)$—$C_{1-6}$ alkyl;
  (c)

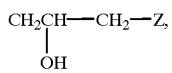

wherein Z is $C_{1-6}$ alkyl or O—$C_{1-6}$ alkyl;
  (d) aryl; or
  (e) heterocycle;
B is a single bond, OH or halo;
C is —OH, —$CH_2$— or forms a 5-membered lactone or lactam ring with D; and
D is:
  (i) —OH, —$CH_2$-halo, —CH(O)—, —COOH, —C(O)—O—$C_{1-6}$ alkyl, —$(CH_2)_n$—, —CHOH—, wherein n is an integer and is 1,2, or 3; or
  (ii) forms a 5-membered lactone or lactam ring with D;
E is —H or —$CH_3$; and
F is —OH or —$OCH_3$, or pharmaceutically acceptable salts thereof, and a pharmaceutically acceptable carrier, said composition useful in the treatment of neoplastic diseases, with the proviso that the formula excludes noscapine of the structure

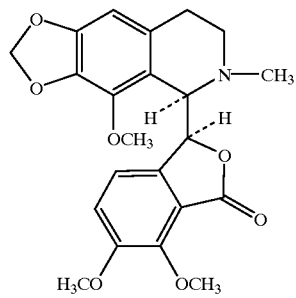

In the present invention, one preferred compound is:

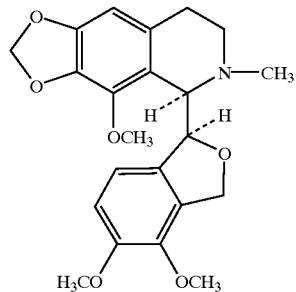

or pharmaceutically acceptable salt thereof.

The present invention also relates to a method for the treatment of neoplastic diseases, comprising administering to a mammal in need of such treatment an effective amount of a composition comprising a compound of the formula

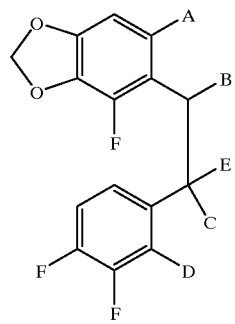

wherein: A is (i)

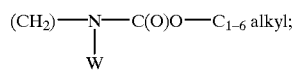

and W is $C_{1-6}$ alkyl;
  (ii)

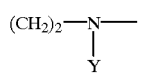

and forms a six membered ring
    with B, said ring containing one nitrogen;
Y is
  (a) $C_{1-6}$ alkyl or H;
  (b) $C(O)$—$C_{1-6}$ alkyl;
  (c)

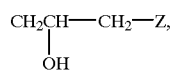

wherein Z is $C_{1-6}$ alkyl or O—$C_{1-6}$ alkyl;
  (d) aryl; or
  (e) heterocycle;
B is a single bond, OH or halo;
C is —OH, —$CH_2$— or forms a 5-membered lactone or lactam ring with D; and
D is:
  (i) —OH, —$CH_2$-halo, —CH(O)—, —COOH, —C(O)—O—$C_{1-6}$ alkyl, —$(CH_2)_n$—, —CHOH—, wherein n is an integer and is 1,2, or 3; or
  (ii) forms a 5-membered lactone or lactam ring with D;
E is —H or —$CH_3$; and
F is —OH or —$OCH_3$, or pharmaceutically acceptable salts thereof, and a pharmaceutically acceptable carrier, said composition useful in the treatment of neoplastic diseases, with the proviso that the formula excludes noscapine of the structure

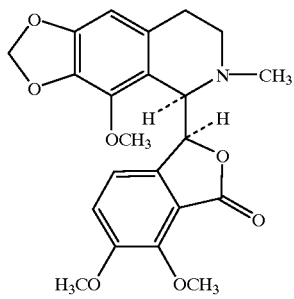

In the method of the present invention, one preferred compound is

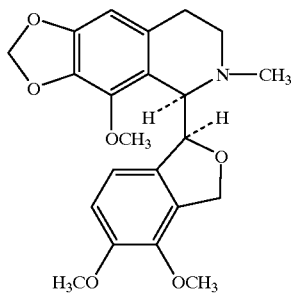

or pharmaceutically acceptable salts thereof.

The compounds of the present invention, may have asymmetric centers and occur as racemates, racemic mixtures and as individual diastereomers or enantiomers, with all isomeric forms being included in the present invention.

When any variable (e.g., W, Y, A, B, C, etc.) occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl) "Halo" as used herein means fluoro, chloro, bromo and iodo. As used herein, with exceptions as noted, "aryl" is intended to mean phenyl (Ph) or naphthyl.

The term heterocycle or heterocyclic, as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include but are not limited to piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl.

The pharmaceutically-acceptable sats of the compounds of the present invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methansulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Synthesis of Noscapine

Noscapine is an alkaloid occurring in abundance in the opium plant, *Papaver somniferum L. papaveraceae*. It can be extracted from the water-insoluble residue remaining from the processing of opium in the commercial synthesis of morphine. It is readily available commercially in large quantities at low cost, from e.g., Aldrich Chemical Co., or Sigma Chemical Co. Noscapine can be separated from other opium alkaloids by the procedure according to Al-Yuhya, M. A. et al., in K. Florey (Ed.) Analytical Profiles of Drug Substances, Vol. 11 Academic Press 1982, pp. 407–461, or Sim, S. K. "Medicinal Plant Alkaloids," 2nd Ed. Un. Toronto Press 1970, p. 70.

Chemical synthesis of noscapine 1 is less desirable, although feasible. See, for example, Fleischhacker, W. et al, Chem. Monthly 120, 765 (1989); Shono, T. et al. Tetrahedron Lett. 21, 1351 (1990).

There are a variety of methods to synthesize noscapine. A one step synthetic reaction was published by W. H. Perkin and R. Robinson, *J. Chem. Soc.*[London], 99, 775 (1911). However, this method gave low yield and racemic mixtures. The reaction is shown as follows:

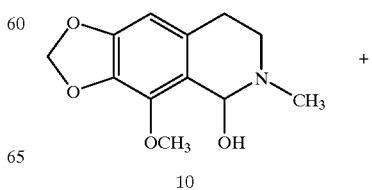

10

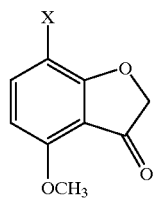

(X = H, Cl, Br, NO$_2$)

11

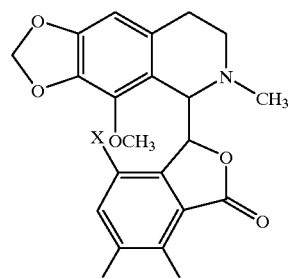

(X = H, Cl, Br, NO$_2$)

12

A second method was published by Von P. Kereks and R Bognar. *J. Prakt. Chem.* 313, 923–928 (1971). In this method, 2-(3'-methoxy-4',5'-methylenedioxy-phenyl) ethylamine 13 reacts with meconine-3-carbonyl chloride 14 in benzene to gove N-(β-3-methoxy-4,5-methylenedioxyphenylethyl)-mekonine-3-carbonylamide 15 with a yield of 86.6%. Compound 15 was cyclized by boiling with POCl$_3$ for 5 hr to produce compounds 16 and 17 with a yield of 46.7%. Compounds 16 and 17 are two isomers from cyclization of compound 15. These two isomers are reduced by either H$_2$/PtO$_2$ in acetic acid, or NaBH$_4$ in methanol. The reduced compound 18 was methylated by boling with the mixture of HCHO and HCOOH, to produce noscapine 1 with a yield of 20.3%.

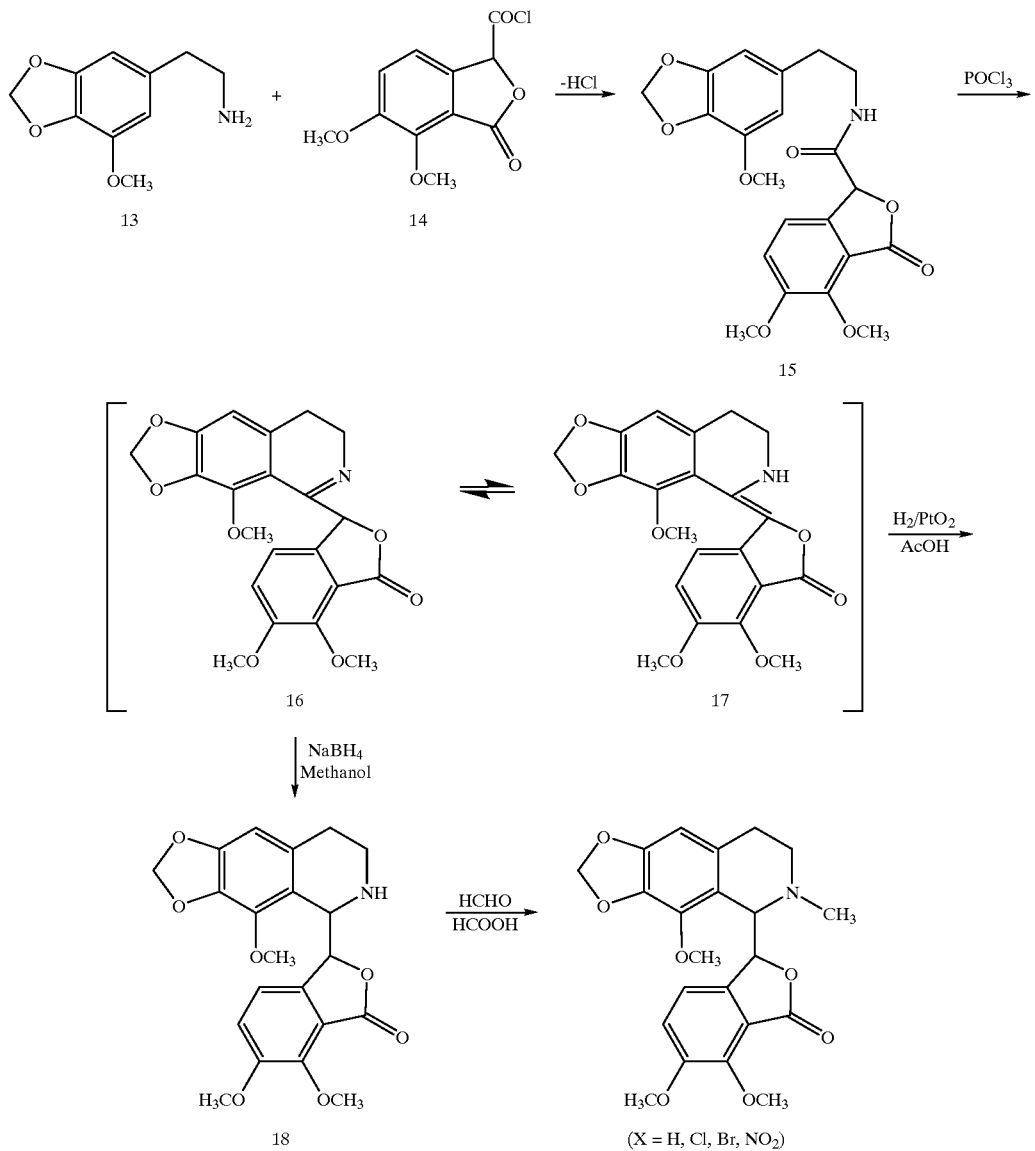

The compounds of the present invention are useful in the treatment of tumor cells and a variety of cancers, including but not limited to cancer of the colon, non-small cell lung cancer, cancer of the brain, ovarian cancer, cancer of the kidney, cancer of the prostate, leukemia, breast cancer, cancer of the bladder. For most of these kinds of neoplastic diseases, applicants have tested a variety of cell lines with noscapine, or derivatives thereof.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating tumor cells and related cancers. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleaginous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitble non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable nonirritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, compound 4 is effectively treated by the administration of from 10 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

EXAMPLE 1

Synthesis of Noscapine

Noscapine 1 was synthesized by the methods of Shono, T. et al., Tetahedron Lett. 21, 1351 (1980); Fleishchacker, W. et al., Monatshefte fur Chemie 120, 765 (1989); Sam, J. et al., J. Pharm. Sci. 57: 1755 (1968); Al-Yuhya, M. A. et al., in K. Florey Ed.) Analytical Profiles of Drug Substances, Vol. 11 Academic Press 1982, pp. 407–461; Battersby, A. R. et al., Tetrahedron Lett. 11, 669 (1965). It is readily available in large quantities from a variety of commercial sources, e.g. Aldrich Chemical Co. or Sigma Chemical Co.

NMR data for (S, R)-Noscapine:

$^1$H NMR (CDCl$_3$, 300 MHz): δ 6.95 (d, J=8.1 Hz, 1 H), 6.27 (s, 1 HI), 6.07 (d, J=8.4 Hz, 1 H), 5.90 (s, 2 H), 5.55 (d, J=3.9 Hz, 1 H), 4.37 (d, J=4.2 Hz, 1H), 4.06 (s, 3 H), 4.00 (s, 3 H), 3.83 (s, 3 H), 2.60 (m, 1 H), 2.52 (s, 3 H), 2.38–2.27 (m, 2 H), 1.94–1.87 (m, 1 H). $^{13}$C NMR(CDCl$_3$, 75.5 MHz): δ 168.0, 152.1, 148.3, 147.5, 140.9, 140.3, 133.9, 131.9, 120, 118.0, 117.6, 116.9, 102.2, 100.7, 81.7, 62.1, 60.7, 59.3, 56.7, 49.9, 46.2, 27.9.

EXAMPLE 2

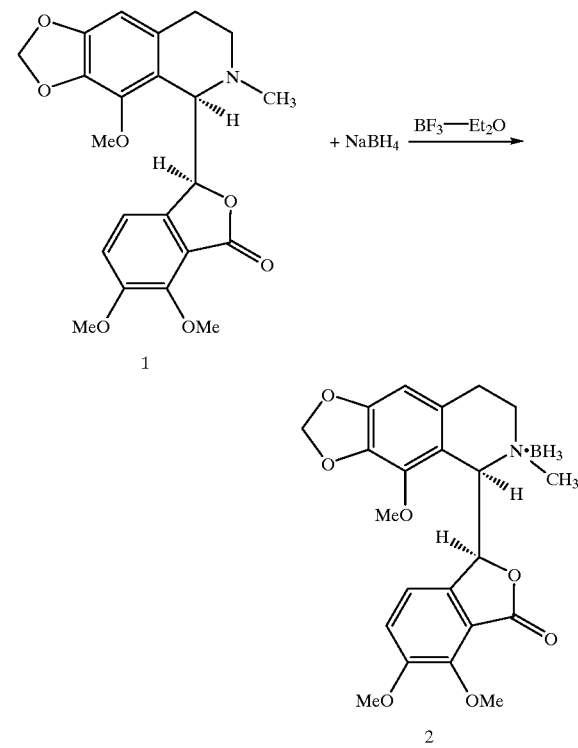

The synthesis of borane-(S, R)-noscapine complex (2):

(S, R)-Noscapine 1 (830 mg, 2.0 mmol, 1.0 equiv.) was dissolved in 10 mL of BF$_3$-Et$_2$O. This solution was dropped slowly at 0° to a solution of NaBH$_4$ (150 mg, 4.0 mmol, 2.0 equiv.) in 14 mL dry THF and stirred at 0° for 1 h under N$_2$. Then it was refluxed for 2 h. After cooling to room temp, the solution was poured into ice water and extracted with CHCl$_3$ (70 mL×2). The organic phase was washed with brine, dried with MgSO4 and concentrated. The resulting oil was purified by flash chromatography (SiO$_2$, 3×15 cm, 50% EtOAc in hexane) to give 2 as a white solid (444 mg, 52%). TLC (silica gel, 65% EtOAc in hexane, R$f$=0.75); $^1$H NMR (CDCl$_3$, 300 MHz): δ 7.41 (d, J=8.1 Hz, 1 H), 7.31 (d, J=8.1 Hz, 1H), 6.83 (s, 1 H), 6.33 (s, 1 H), 5.81 (dd, J=12.9 Hz, 0.9 Hz, 2 H), 4.54 (s, 1 H), 3.99 (s, 3 H), 3.92 (s, 3 H), 3.73 (m, 1 H), 3.20 (s, 3 H), 3.15 (m, 2 H), 2.93 (m, 1 H), 2.61 (s, 3H).

EXAMPLE 3

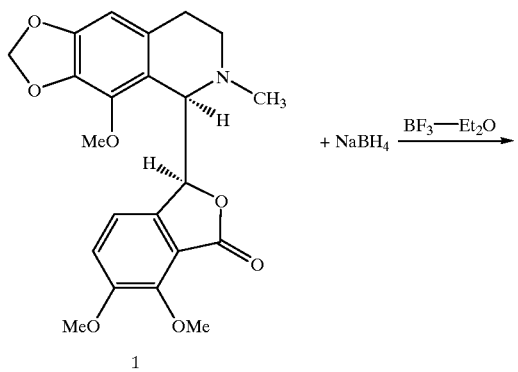

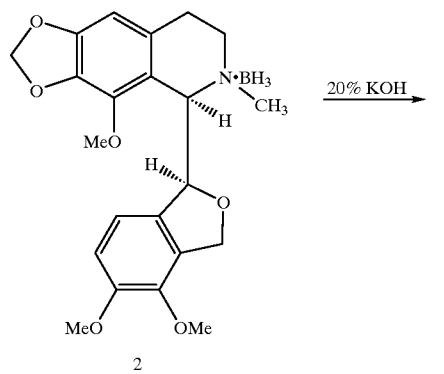

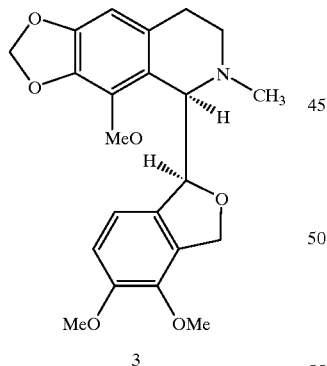

Compound 3 and 4 were prepared by literature method Prior, S.; Wiegrebe, W. *Arch. Pharm.* 1983, 316, 737.

The synthesis of 1,3-dihydro-4,5-dimethoxy-1-[1-(8-methoxy-2-methyl-6,7-methylenedioxy-1,2,3,4-tetrahydroisoquinolinyl)] isobenzofuran-BH$_3$ (3):

(S,R)-Noscapine (830 mg, 2.0 mmol, 1.0 equiv.) was dissolved in 10 mL of BF$_3$-Et$_2$O. This solution was dropped slowly at 0° C. to a solution of NaBH (150 mg, 4.0 mmol, 2.0 equiv.) in 18 mL dry THF and stirred at 0° C. for 1 h under N$_2$. Then it was refluxed for 4 h. After cooling to room temp, the solution was poured into ice water and extracted with CHCl$_3$ (70 mL×2). The organic phase was washed with brine, dried with MgSO$_4$ and concentrated. The resulting oil was purified by flash chromatography (SiO$_2$, 3×15 cm, 50% EtOAc in hexane) to give 3 as a white solid (686 mg, 83%). TLC (silica gel, 50% EtOAc in hexane, R$f$=0.80); IR (CH$_2$Cl$_2$, NaCl, cm$^{-1}$) 2371 (s), 1616 (w). $^1$H NMR (CDCl$_3$, 300 MHz): δ 7.15 (d, J=8.4 Hz, 1 H), 6.93 (d, J=8.1 Hz, 1 H), 6.57 (br s, 1 H), 6.33 (s, 1 H), 5.79 (AB, J=1.5 Hz, 1 H), 5.74 (AB, J=1.5 Hz, 1 H), 4.81 (d, J=12.0 Hz, 1 H), 4.34 (s, 1 H), 4.07 (dd, J=12.3 Hz, 2.7 Hz, 1 H), 3.85 (s, 3 H), 3.71 (s, 3 H), 3.16 (s, 3 H), 3.05–2.81 (m, 4 H), 2.53 (s, 3 H). HRMS (FAB) Calcd for C$_{22}$H$_{28}$BLiNO$_6$ (M+Li)$^+$: 420.2170, Found 420.2173.

The synthesis of 1,3-dihydro-4,5-dimethoxy-1-[1-(8-methoxy-2-methyl-6,7-methylenedioxy-1,2,3,4-tetrahydroixoquinolinyl)]isobenzofuran (4):

Compound 3 (450 mg, 1.10 mmol) was refluxed in 15 mL of 20% aqueous KOH solution for 2 h. The reaction mixture was cooled to room temp, neutralized with 2 N HCl to PH=7 and extracted with CHCl$_3$. The organic phase was washed with brine, dried with MgSO4 and concentrated. Compound 4 was crystallized from Et$_2$O (220 mg, 50%). $^1$H NMR (CDCl$_3$, 300 MHz): delta 6.72 (d, J=8.4 Hz, 1 H), 6.32 (s, 2 H), 5.88 (m, 2 H), 5.63 (br s, 1 H), 5.02 (br s, 2 H), 4.40 (br s, 1H), 3.82 (s, 3 H), 3.81 (s, 3 H), 3.75 (s, 3 H), 3.14 (br s, 1 H), 2.64 (br s, 3 H),2.60–2.43 (m, 3H).

EXAMPLE 4

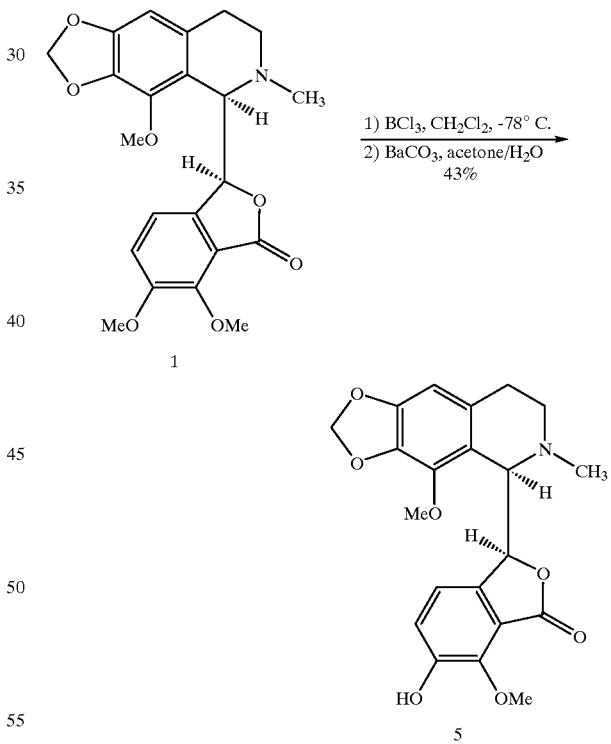

The synthesis of compound 5:

(S,R)-Noscapine (826 mg, 2.0 mmol, 1.0 equiv.) was dissolved in 25 mL of CH$_2$Cl$_2$. This solution was added dropwise to a 1.0 M solution of borane trichloride in CH$_2$Cl$_2$ (8.0 mL, 8.0 mmol, 4.0 equiv.) at —78° C. After 5 h, the reaction was quenced with saturated aqueous NaHCO3 (10 mL) and warmed to room temp. The reaction mixture was extracted with EtOAc (50 mL×3), the combined organic phases were washed with brine (40 mL), dried with MgSO$_4$ and concentrated.

The obtained white solid was dissolved in acetone (50 mL) and H$_2$O (25 mL). This solution was treated with barium carbonate (1.55 g, 7.84 mmol) and refluxed for 3 h. After cooling to room temp, the reaction mixture was filtered. The filtrate was treated with 1 N HCl until PH=2, then extracted with EtOAc (50 mL×3). The combined extracts were washed with brine, dried over MgSO$_4$ and concentrated. Crystallization (CH$_2$Cl$_2$-Et$_2$O) was performed for the resulting off-white solid to give 5 as a silver gray solid (340 mg, 43%). IR (CH$_2$Cl$_2$, NaCl, cm$^{-1}$) 3431 (s), 1767 (s). $^1$H NMR (CDCl$_3$, 300 MHz): δ 7.57 (br s, 1 H), 7.27 (br s, 1H), 6.57 (br s, 1 H), 6.33 (s, 1 H), 5.82 (s, 1 H), 5.78 (s, 1H), 5.11 (br s, 1 H), 4.08 (br s, 1 H), 3.94 (s, 3 H), 3.87 (s, 3 H), 3.33 (m, 1 H), 3.20 (s, 3 H), 3.00 (m, 1 H), 2.82 (m, 2 H). $^{13}$C NMR (CDCl$_3$, 75.5 MHz): δ 166.3, 152.4, 150.1, 147.3, 139.8, 138.9, 133.4, 126.2, 119.3, 118.8, 116.9, 106.7, 102.3, 100.9, 78.5, 61.9, 58.2, 56.8, 45.2, 39.9, 21.4.

EXAMPLE 5

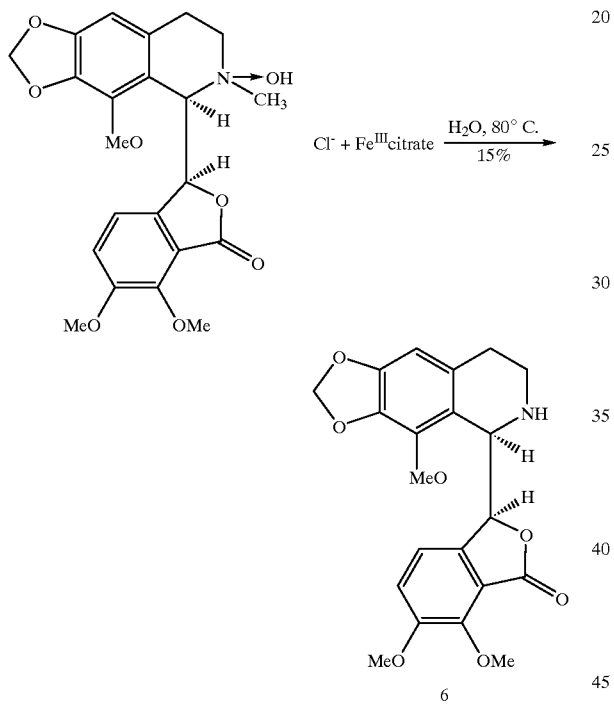

Ferric citrate (10.5 g) was dissolved in 200 mL of H$_2$O. Citric acid was added to make pH=2. This solution was added to noscapine N-oxide HCl salt (6.0 g)[Uhrin, D. et al., Collect. Czech. Chem. Commun. 54:498(1989)] and the mixture was heated to 85° C. for 3 h. After cooling to room temp, the solution was treated with saturated Na$_2$CO$_3$ solution until pH=9 and extracted with CHCl$_3$ (200 mL×4). The combined organic phases were washed with brine, dried with anhydrous MgSO$_4$ and concentrated. The resulting oil was purified by flash chromatography (SiO$_2$, 3×25 cm, 75% EtOAc in hexane) to give 6 as a yellow oil (793 mg, 15%). TLC (silica gel, 75% EtOAc in hexane, R$_f$=0.25); IR (CH$_2$Cl$_2$, NaCl, cm$^{-1}$) 3370 (w), 1758 (s); $^1$H NMR (CDCl$_3$, 300 MHz):): δ 6.92 (d, J=8.1 Hz, 1 H), 6.29 (s, 1 H), 5.93–5.91 (m, 3 H), 5.87 (d, J=3.9 Hz, 1 H), 4.80 (d, J=3.9 Hz, 1 H), 4.04 (s,3 H), 4.02 (s, 3 H), 3.80 (s, 3 H), 2.59–2.55 (m, 1 H), 2.50–2.38 (m, 1 H), 2.30–2.22 (m, 1 H), 2.15–2.07 (m, 1 H), 1.96 (br s, 1 H). $^{13}$C NMR (CDCl$_3$, 75.5 MHz):): δ 168.4, 152.1, 148.3, 147.8, 141.0, 140.3, 134.1, 131.9, 119.5, 118.4, 117.5, 116.9, 103.1, 100.7, 80.6, 62.2, 59.4, 56.6, 52.7, 39.5, 29.6. HRMS (FAB) Calcd for C$_{21}$H$_{21}$LiNO$_7$ (M+Li)$^+$: 406.1478, Found 406.1477. Anal. Calcd. for C$_{21}$H$_{21}$NO$_7$: C, 63.15; H, 5.30; N, 3.51. Found: C, 63.35; H, 5.45; N, 3.42.

EXAMPLE 6

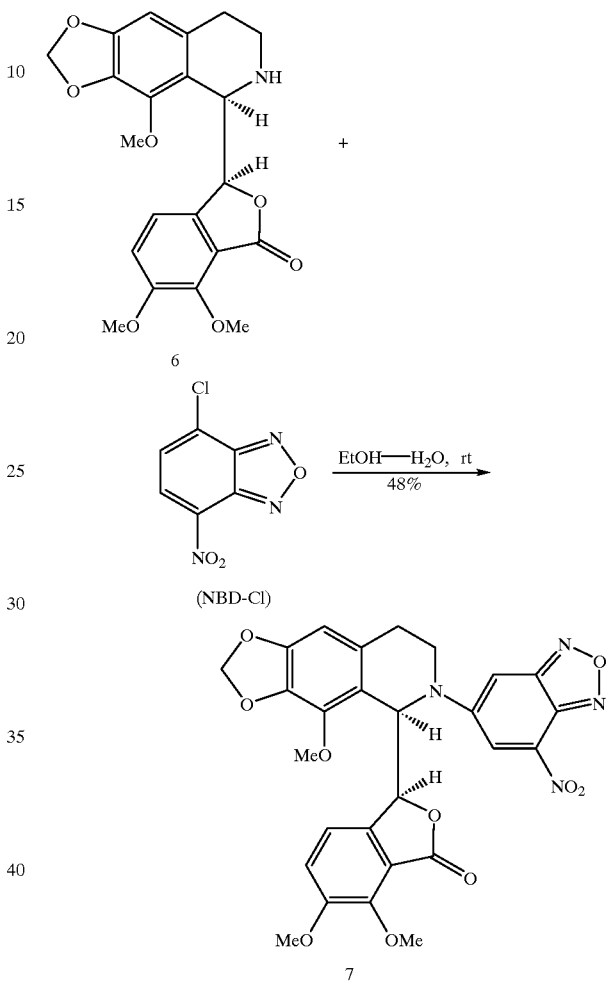

To an ETOH (15 mL) solution of amine 6 (160 mg, 0.40 mmol, 1.0 equiv.) was added 30 mL of Na$_2$B$_4$O$_7$ (1.14 g) buffer and NBD-CL (80 mg, 0.4 mmol, 1.0 equiv.). The reaction mixture was stirred at room temp for 15 h. Evaporation of ETOH left a dark orange slurry which was extracted with CHCl$_3$ (70 mL×2). The combined organic phases were washed with brine, dried with MgSO$_4$ and concentrated. The resulting green oil was purified by flash chromatography (SiO$_2$, 3×1 5 cm, 65% EtOAc in hexane) to give an orange solid which was recrystallized from CH$_2$Cl$_2$ and hexane to give 7 as an orange crystal (108 mg, 48%). TLC (silica gel, 65% EtOAc in hexane, R$_f$=0.65); mp=194–195° C. (CH$_2$Cl$_2$/hexane); IR (CH$_2$Cl$_2$, NaCl, cm$^{-1}$) 1765 (s), 1616 (m), 1540 (s), 1500 (s), 1287 (s), 1261 (m). $^1$H NMR (CDCl$_3$, 300 MHz):): δ 8.53 (d, J=9.0 Hz, 1 H), 7.41 (br d, J=7.8 Hz, 1 H), 7.29 (d, J=8.4 Hz, 1 H), 7.00 (br s, 1 H), 6.48 (d, J=2.7 Hz, 1 H), 6.44 (s, 1 H), 6.04 (d, J=2.7 Hz, 1 H), 5.90 (d, J=7.5 Hz, 2 H), 4.02 (s, 3 H), 3.95 (s, 3 H), 3.81 (m, 1 H), 3.76 (s, 3 H), 3.70–3.50 (m, 2 H), 3.02–2.93 (m, 1 H). $^{13}$C NMR (CDCl$_3$, 75.5 MHz):): δ 166.7, 152.8, 149.6, 147.9, 145.1, 145.0, 144.7, 139.5, 138.7, 135.3, 133.7, 130.4, 123.7, 119.0, 118.7, 118.1, 113.4, 102.9, 102.4, 100.9, 81.9, 62.2, 59.1, 58.1, 56.8, 46.5, 27.8. HRMS (FAB) Calcd for $C_{27}H_{22}LiN_4O_{10}$ (M+Li)+: 569.1496, Found 569.1472. Anal. Calcd. for $C_{27}H_{22}N_4O_{10}$: C, 57.65; H, 3.91; N, 9.96. Found: C, 57.85; H, 4.04; N, 9.81.

EXAMPLE 7

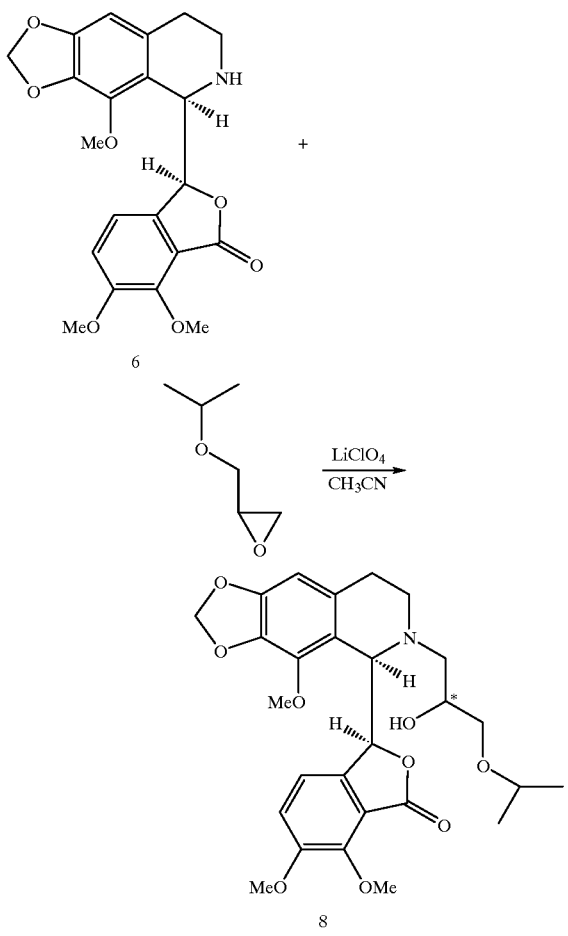

A $CH_3CN$ (2 mL) solution of glycidyl isopropyl ether (50 μL, 0.40 mmol, 1.0 equiv.) was treated with anhydrous $LiClO_4$ salt (43 mg, 0.40 mmol, 1.0 equiv.) and stirred for about 10 min. until a clear solution was observed. This solution was treated with an $CH_3CN$ (3 mL) solution compound 6 (160 mg, 0.40 mmol, 1.0 equiv.) at room temp. The mixture was refluxed for 24 h, cooled to room temp., washed with $H_2O$ and extracted with $Et_2O$ (40 mL×3). The combined organic phases were washed with brine, dried with $MgSO_4$ and concentrated. The resulting orange oil was purified by flash chromatography ($SiO_2$, 2×15 cm, 50% EtOAc in hexane) to give 8 as a yellow oil which is a mixture of the two diasteoromers (1:1 ratio, 172 mg, 83%). TLC (silica gel, 50% EtOAc in hexane, $R_f$=0.50); IR ($CH_2Cl_2$, NaCl, cm$^{-1}$) 3450 (m), 1761 (s), 1498 (m), 1478 (m). $^1$H NMR ($CDCl_3$, 300 MHz):): δ 6.96 (d, J=8.4 Hz, 2 H), 6.30 (s, 2 H), 6.24 (t, J=8.4 Hz, 2 H), 5.90 (s, 4 H), 5.73 (d, J=4.5 Hz, 1 H), 5.67 (d, J=4.2 Hz, 1 H), 4.47 (d, J=4.2 Hz, 1 H), 4.42 (d, J=4.5 Hz, 1 H), 4.06 (s, 3 H, 4.05 (S. 3 H, 3.97 (s, 3 H), 3.96 (s, 3H), 3.82 (s, 6 H), 3.56 (d of sept, J=6.0 Hz, 2 H), 3.41 (m, 4 H), 3.0 (br s, 2 H), 2.74–2.00 (m, 14 H), 1.1 2 (t, J=5.7 Hz, 12 H). $^{13}$C NMR ($CDCl_3$, 75.5 MHz):): δ 167.9, 167.8, 152.2 (2 C), 148.5 (2 C), 148.1 (2 C), 141.2, 141.0, 140.5, 140.4, 133.8, 133.7, 130.9, 130.5, 119.3, 119.0, 118.4(2 C), 117.5 (2 C), 116.3, 115.8, 102.7, 102.6, 100.7, 100.6, 80.8, 80.1, 71.9, 71.8, 70.4, 70.1, 68.0, 67.8, 62.3, 62.2, 60.5 (2 C), 59.4, 59.2, 58.6, 58.5, 56.7 (2 C), 46.2, 44.7, 24.8, 24.3, 22.0 (2 C), 21.9 (2 C). Anal. Calcd. for $C_{27}H_{33}NO_9$: C, 62.90; H, 6.45; N, 2.72. Found: C, 62.97; H, 6.45; N, 2.64.

EXAMPLE 8

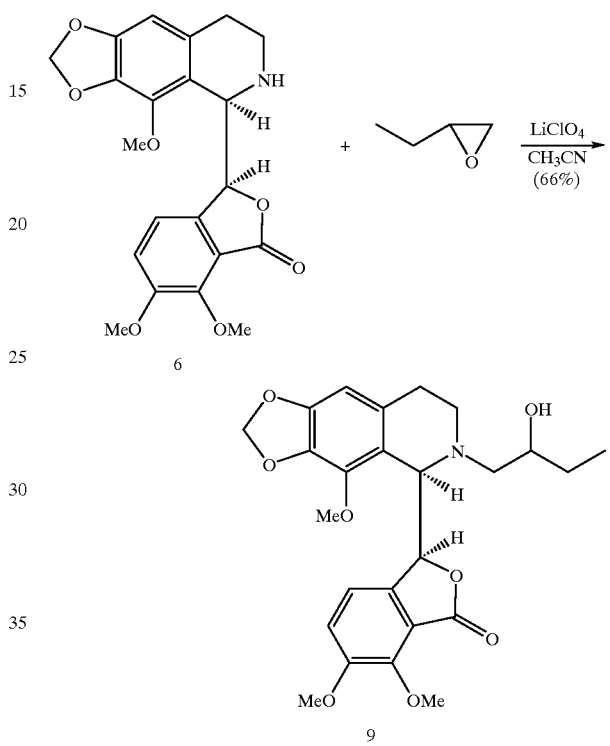

An $CH_3CN$ (2 mL) solution of 1,2-epoxybutane (114 μL, 1.32 mmol, 3.3 equiv) in a sealed tube was treated with anhydrous $LiClO_4$ salt (43 mg, 0.40 mmol, 1.0 equiv) and stirred for 10 min until a clear solution was observed. This solution was treated with an $CH_3CN$ (3 mL) solution of compound 6 (160 mg, 0.40 mmol, 1.0 equiv) at room temp. The mixture was heated at 115° C. for 10 h, cooled to room temp, washed with $H_2O$ and extracted with $Et_2O$ (50 mL×3). The combined organic phases were washed with brine, dried with $MgSO_4$ and concentrated. The resulting yellow oil was purified by flash chromatography (SiO2, 2×15 cm, 65% EtOAc in hexane) to give 9 as a light yellow oil which is a mixture of the two diasteoromers (1:1 ratio, 125 mg, 66%). TLC (silica get, 65% EtOAc in hexane, $R_f$=0.60); IR ($CH_2Cl_2$, NACl, cm$^{-1}$) 3523 (s), 1758(s), 1622 (m). $^1$H NMR ($CDCl_3$, 300 MHz):):): δ 6.99 (d, J=8.1 Hz, 2 H), 6.31 (s, 1 H), 6.30 (s, 1 H), 6.26 (d, J=8.4 Hz, 1 H), 6.25 (d, J=8.4 Hz, 1 H), 5.90 (s, 4 H), 5.79 (d, J=4.5 Hz, 1 H), 5.68 (d, J=3.9 Hz, 1 H), 4.48 (d, J=3.9 Hz, 1 H), 4.40 (d, J=4.5 Hz, 1 H), 4.07 (s, 3 H), 4.06 (s, 3 H), 3.98 (s, 6 H), 3.83 (s, 6 H), 3.66–3.53 (m, 2 H), 3.20 (br s, 2 H), 2.68–2.38 (m, 8 H), 2.23–2.10 (m, 4 H), 1.42 (m, 4 H), 0.95 (t, J 6.9 Hz, 3 H), 0.93 (t, J=7.2 Hz, 3 H). $^{13}$C NMR ($CDCl_3$, 75.5 MHz):): δ 168.0, 167.7, 152.3, 152.2, 148.6 (2 C), 148.2, 148.1, 141.2, 140.9, 140.6, 140.3, 133.9, 133.7, 130.9, 130.1, 119.3, 118.8, 118.5 (2 C), 117.4 (2 C), 116.4, 115.4, 102.8, 102.5, 100.7, 100.6, 81.1, 79.6, 68.9, 68.7, 62.5, 62.3, 62.2, 61.3, 61.2, 59.3, 59.2, 57.5, 56.7 (2 C), 46.4, 44.0, 27.5, 27.1, 25.1, 23.7, 10.0, 9.8. Anal. Calcd. for $C_{25}H_{29}NO_8$: C, 63.68; H, 6.20; N, 2.97. Found: C, 63.68; H, 6.18; N, 2.90.

EXAMPLE 9
Noscapine Arrests Hela and Thymocyte cells at M Phase

Hela cells were grown in DMEM supplemented with 10% fetal calf serum, 1 mM L-glutamine and 1% penicillin/streptomycin. The tumor cell line E.G7-OVA (H-$2^b$) [Moore, M. W., et al., Cell 54, 777 (1988)] was grown in RPMI 1640 with 10% fetal calf serum, 1% sodium pyruvate, 1 mM L-glutamine, 0.1% gentamycin, 50 μM β-mercaptoethanol. Cells were grown at 37° C. in a 5% $CO_2$ atmosphere. Cell viability was assessed by trypan blue exclusion analysis. Cell numbers were determined using a hemacytometer. C57BL/6 (H-$2^b$) mice, 8 to 12 weeks of age, were obtained from Harian Sprague Dawley, Inc. (Indiananapolis, Ind.). Mice were maintained on standard laboratory chow and water ad libitum in a temperature and light controlled environment. For immunofluorescence, both Hela and thymocyte cells were treated identically except the Hela cells were grown onto glass coverslips while EL4 thymocytes were put on glass coverslips after fixation. Cells in 10 ml medium were incubated with 2 μl DMSO or 20 μM Noscapine (2 μl 0.1 M DMSO solution) respectively. After 24 hr, cells were fixed with cold (–20° C.) methanol for 5 min., then rehydrated by PBS for 1 min. Nonspecific sites were blocked by incubating with 200 μl of 1% bovine serum albumin (BSA) in phosphate buffered saline (PBS) at 37° C. for 15 minutes. A mouse monoclonal antibody against α-tubulin was diluted 1:200 in PBS containing 1% BSA and incubated (200 μl) with the coverslips at 37° C. for 1 hr. Then cells were washed with 1% BSA-PBS solution for 10 min. at room temperature before incubating with a 1:200 dilution of a rhodamine labeled goat anti-mouse IgG antibody at room temperature for 45 min., then the coverslips were rinsed by 1% BSA/PBS solution for 10 min. and labeled by DAPI (4', 6-diamino-2-phenyliudole) for another 10 min. at room temperature. The coverslips containing the cells were then mounted with a solution containing 0.01% 1,4-diazobicyclo (2,2,2) octane. Cells were examined with a fluorescence microscope. The flow cytometric evaluation of the cell cycle status was performed according to a modification of as described in Empey, D. W., et al., Eur. J. Clin. Pharmacol. 16, 393 (1979). Briefly, untreated or noscapine-treated cells were centrifuged, washed twice with ice-cold PBS, and fixed in 70% ethanol. Tubes containing the cell pellets were stored at –20° C. for at least 24 hr. Following this, the cells were centrifuged at 1000×g for 10 min. and supernatant was discarded. The pellets were resuspended in 30 μl phosphate-citrate buffer at room temperature for 30 min. Cells were then washed with 5 ml PBS and incubated with propidium iodide and RNase (20 mg/ml PI and 20 mg/ml RNase A in PBS) for 30 min. The samples were read on a cytometer.

Results show that by immunofluorescence, with an antibody specific for alpha-tubulin, that after treatment with noscapine, microtubule arrrays are arrested in M phase in Hela and thermocyte cells. Flow cytometric analysis of DNA content showed consistent results.

EXAMPLE 10
Noscapine Initiates Apoptosis

Oligonucleosomal fragmentation of genomic DNA was determined according to Walton, M. I. et. al., Cancer. Res. 53, 1853 (1993). An aliquot of 3.3×$10^6$ cells in 10 ml medium was incubated with 20 μM Noscapine (2 g 0.1 M DMSO solution) for different time periods ranging from 0 to 24 hr. At the end of incubation, cells were pelleted and washed twice with ice-cold PBS, and lysed in 250 μl 1% (v/v) NP-40 detergent containing 0.5 mg/ml proteinase K in PBS solution on ice for 60 min. Samples were centrifuged, and the supernatants were removed and incubated with 5 μl 10 mg/ml Rnase A at 37° C. for 40 min. An aliquot of 1 ml anhydrous ethanol was added, tubes were placed at –20° C. for 20 min., then centrifuged to pellet DNA. After the samples were dry, the same amount of DNA (10 μg) was electrophoresed at 80V for 3 hr. through a 2% agarose gel containing ethidium bromide in TAE buffer. DNA bands were visualized under HV light. A 123 bp DNA ladder was used as molecular size marker.

Morphological changes in the nuclear chromatin of cells undergoing apoptosis were detected by staining with 4', 6-diamidino-2-phenylindole (DAPI). In brief, 0.5×$10^6$ to 3×$10^6$ cells were fixed with 4% glutaraldehyde, 0.2% Triton x-100, in PBS and incubated at room temperature for 10 min., then centrifuged at 1000×g for 10 Min., resuspended in 20 μl 0.1% DAPI ethanol. Following 15 min. incubation at room temperature, a 10 μl aliquot was placed on a glass slide, and 400 cells per slide were scored for the incidence of apoptotic chromatin changes with a fluorescence microscope. A TdT-Mediated dUTP nick end labeling assay is used according to Gorczyca, W. et al., Cancer Res. 53, 1945 (1993) and Gavrieli, Y. et al., J. Cell Bio. 119, 493 (1992). An aliquot of 2×$10^6$ cells in 10 ml medium were respectively incubated with 2 μl DMSO and 20 μM noscapine (2 μl 0.1 M DMSO solution) for 24 hr. Cells were pelleted and washed with ice-cold PBS twice, lymphocyte cells were fixed in 4% paraformaldehyde in PBS and air dried. The slides were rinsed with PBS and incubated with blocking solution (0.3% $H_2O_2$ in methanol) for 30 min. at room temperature. The slides were rinsed with PBS again and incubated in permeability solution (0.1% Triton x-100 in 0.1% sodium citrate) on ice for 2 min. Then the slides were washed twice with PBS, then 50 μl nick end labeling assay reaction mixture was added on samples and the slides were incubated in a humidified chamber for 60 min. at 37° C. After the slides were rinsed with PBS, 50 μl converter-POD solution was added on samples and incubated for 30 min. at 37° C. The slides were rinsed with PBS for 3 times, then 60 μl DAB substrate solution was added on the samples, and the slides were incubated at room temperature for 10 min. After the slides were ringed with PBS for another 3 times, coverslips were mounted and analyzed with a light microscope.

Results show progressive DNA degradation with increasing time of noscapine treatment, as measured by gel electrophoresis of fragmented genomic DNA, or by staining of treated cells.

EXAMPLE 11
Inhibition of Tumor Growth by Noscapine

C57BL/6 mice were injected subcutaneously in the right flank with 2×$10^6$ E.G7-OVA cells. Three days later, mice were injected intraperitoneally, every day for three weeks, either with 200 μl saline (n=10), or with 3 mg noscapine dissolved in 200 μl saline (n=10),. Third group of mice (n=10) was fed 3 mg noscapine via intragastric (i.g.) intubation using a 1 ml syringe fitted with a 20 gauge stainless steel ball point needle. After three weeks, all mice were sacrificed by cervical dislocation. Tumors were removed and weighted. Tumor weights were individually plotted and comparisons between control and treatment groups were analyzed by the Student's t test. Statistical differences were considered significant if p values were less than 0.01. Results showed that mice treated with noscapine had significantly reduced tumor weight.

EXAMPLE 12

Noscapine Causes Apoptosis in Solid Lymphoid Tumors Induced in Mice

Microscopic examination of Haemotoxline and Eosine stained cells showed many cells in noscapine treated mice with apoptotic morphologies.

EXAMPLE 13

Noscapine Induces Conformational Change Upon Binding Tubulin and Promotes Microtube Assembly Phosphocellulose purified bovine brain tubulin was employed throughout these biophysical experiments. Fluorescence titration for determining binding constants was performed according to Peyrot, V. et al., Biochemistry 31, 11125 (1992). In brief, at room temperature, 2 $\mu$M tubulin in 100 mM PIPES, 2 mM EGTA, 1 mM MgCl$_2$ was excited at 278 nm, and the fluorescence emission spectra were recorded with bandwidths 2 nm. The fluorescence emission intensity of noscapine at this excitation wavelength was negligible and at the concentration of noscapine used it gave no appreciable inner filter effect. The concentration of noscapine was raised in increments of 0.5 $\mu$M, until the decrease in the fluorescence intensity was saturated. The value of the dissociation constant and the number of sites were obtained from Scatchard plots using the equation, $r/[L]_{free}=n/K^d-r/K_d$, where r is the ratio of the concentration of bound ligand to the total protein concentration and n is the number of binding sites. Circular dichroism (CD) spectra measurements were performed in a spectroscometer, in cells (0.1 cm path) at 25° C. Microtubule assembly was recorded on a spectrophotometer with thermocontroler. The cuvettes (0.4 cm path) containing 100 mM PIPES, 2 mM EGTA, 1 mM MgCl$_2$ and 1 mM GTP (G-PEM buffer), and 20 $\mu$M noscapine/DMSO were kept at room temperature before addition of tubulin and shifting to 37° C. Tubulin and noscapine in G-PEM buffer did not show any detectable absorption at 350 nm. The assembly was monitored by measuring the changes in turbidity at 0.5 min. intervals. Noscapine was dissolved in DMSO at 0.8 mM and stocked at 4° C. The final concentration of DMSO was 2.5%.

Results show that noscapine affords fluorescence quenching of tubulin. Scatchard plot analysis showed an apparent dissociation constant (K$_d$) of 1.86±0.34×10$^{-6}$ M and a stoichiometry of 0.95±0.02 noscapine molecule per complex of tubulin subunit. There is also saturation of the noscapine induced quenching in tubulin fluorescence intensity. Noscapine promotes tubulin assembly, as measured by increased absorbance at 350 nm of tubulin when treated with noscapine.

EXAMPLE 14

Initiation of Apoptosis by Noscapine and derivatives

Morphological changes in the nuclear chromatin of HL-60 cells undergoing apoptosis were detected by staining with 4', 6-diamidino-2-phenylindole (DAPI). In brief, 0.5× 10$^6$ to 3×10$^6$ cells were fixed with 4% glutaraledehyde, 0.2% Triton x-100, in PBS and incubated at room temperature for 10 min., then centrifuged at 1000×g for 10 min., resuspended in 20 $\mu$l 0.1% DAPI ethanol. Following 15 min. incubation at room temperature, at 10 $\mu$l aliquot was placed on a glass slide, and 400 cells per slide were scored for the incidence of apoptotic chromatin changes with a fluorescence microscope.

Results show that noscapine, compound 3 and compound 4 initiate apoptosis.

| Compound* | Apoptic Cell Percentage |
|---|---|
| Noscapine, 20 $\mu$M in DMSO | 30, 17† |
| 3, 20 $\mu$m in DMSO | 37, 28 |
| 4, 20 $\mu$M in DMSO | 48, 32 |
| Noscapine, 50 $\mu$M in DMSO | 27 |
| 3, 50 $\mu$M in DMSO | 39 |
| 4, 50 $\mu$M in DMSO | 52 |

*All compounds were incubated with HL-60 cells at the indicated final concentrations for 24 hours.
†Two trials were conducted at 20 $\mu$M, the result for each trial is shown.

While the foregoing specification teaches the principles of the present invention, with examples provided for the purpose of illustration, it will be understood that the practice of the invention encompasses all of the usual variations, adaptations, modifications or deletions as come within the scope of the following claims and its equivalents.

What is claimed is:

1. A method for the treatment of neoplastic diseases, comprising administering to a mammal in need of such treatment an effective amount of a composition comprising a compound of the formula

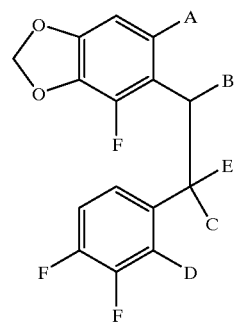

wherein: A is
(i)

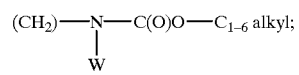

and W is C$_{1-6}$ alkyl; or
(ii)

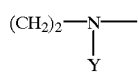

and forms a six membered ring with B, said ring containing one nitrogen;
Y is
(a) C$_{1-6}$ alkyl, or H;
(b) C(O)—C$_{1-6}$ alkyl;
(c)

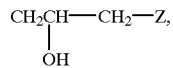

wherein Z is C$_{1-6}$ alkyl or O—C$_{1-6}$ alkyl;
(d) aryl; or
(e) heterocycle;

B is a single bond, OH or halo;

C is —OH, —CH$_2$— or forms a 5-membered lactone or lactam ring with D; and

D is:
  (i) —OH, —CH$_2$—halo, —CH(O)—, —COOH, —C(O)—O—C$_{1-6}$ alkyl, —(CH$_2$)$_n$—, —CHOH—, wherein n is an integer and is 1,2, or 3; or
  (ii) forms a 5-membered lactone or lactam ring with C;

E is —H or —CH$_3$; and

F is —OH or —OCH$_3$, or pharmaceutically acceptable salts thereof, and a pharmaceutically acceptable carrier, said composition useful in the treatment of neoplastic diseases, with the proviso that the formula excludes noscapine of the structure.

2. A method for the treatment of neoplastic diseases, comprising administering to a mammal in need of such treatment an effective amount of a composition comprising a compound of the formula

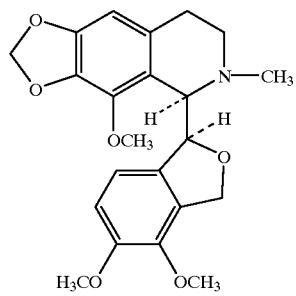

or pharmaceutically acceptable salts thereof, and a pharmaceutically acceptable carrier, said composition useful in the treatment of neoplastic diseases.

3. The method of claim 1, wherein the compound is noscapine.

4. The method of claim 1, wherein the neoplastic disease is selected from the group consisting of cancer of the colon, non-small cell lung cancer, cancer of the brain, ovarian cancer, cancer of the kidney, cancer of the prostate, leukemia, breast cancer, arid cancer of the bladder.

5. A pharmaceutical composition for treatment of neoplastic diseases, comprising an anti-neoplastic effective amount of a compound of the formula

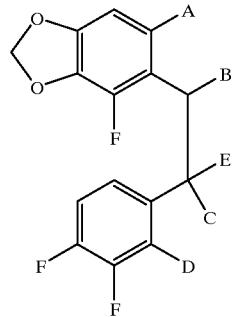

wherein: A is
  (i)

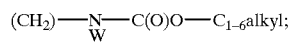

and W is C$_{1-6}$ alkyl; or
  (ii)

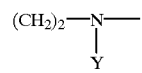

and forms a six membered ring with B, said ring containing one nitrogen;

Y is
  (a) C$_{1-6}$ alkyl, or H;
  (b) C(O)—C$_{1-6}$ alkyl;
  (c)

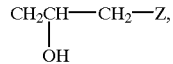

wherein Z is C$_{1-6}$ alkyl or O—C$_{1-6}$ alkyl;
  (d) aryl; or
  (e) heterocycle;

B is a single bond, OH or halo;

C is —OH, —CH$_2$— or forms a 5-membered lactone or lactam ring with D; and

D is:
  (i) —OH, —CH$_2$-halo, —CH(O)—, —COOH, —C(O)—O—C$_{1-6}$ alkyl, —(CH$_2$)$_n$—, —CHOH—, wherein n is an integer and is 1,2, or 3; or
  (ii) forms a 5-membered lactone or lactam ring with C;

E is —H or —CH$_3$, and

F is —OH, or pharmaceutically acceptable salts thereof, and a pharmaceutically acceptable carrier, said composition useful in the treatment of neoplastic diseases, with the proviso that the formula excludes noscapine of the structure

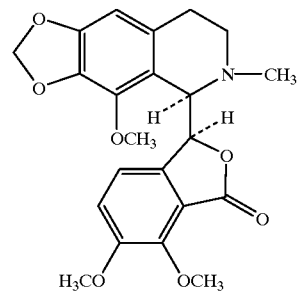

and a pharmaceutically acceptable carrier therefor.

6. The pharmaceutical composition of claim 5, which is an orally administrable suspension or tablet, nasal spray, a sterile injectable preparation, or a suppository.

* * * * *

UNITED STATES PATENT AND TRADEMARK OFFICE
CERTIFICATE OF CORRECTION

PATENT NO. : 6,376,516 B1
DATED : April 23, 2002
INVENTOR(S) : Harish C. Joshi, Keqiang Ye, Judith Kapp and Fugiang Liu It is certified that error appears in the above-identified patent and that said Letters Patent is hereby corrected as shown below:

<u>Title page,</u>
Item [75], Inventors: delete "Ye Keqiang" and insert -- Keqiang Ye --

<u>Column 5,</u>
Line 44, insert a -- ; -- following the word "butyl)"

<u>Column 6,</u>
Line 7, delete "sats" and insert -- salts --

<u>Column 10,</u>
Line 22, delete "(s, 1 HI)" and insert -- (s, 1 H) --

<u>Column 11,</u>
Line 64, delete "NaBH" and insert -- $NaBH_4$ --

<u>Column 15,</u>
Line 65, delete "(s, 3 H," and insert -- (s, 3H)," --

<u>Column 16,</u>
Line 52, delete "(SiO2," and insert -- ($SiO_2$, --
Line 55, delete "get" and insert -- gel --

<u>Column 17,</u>
Line 67, delete "(2 g 0.1 M" and insert -- (2 $\mu$l 0.1 M --

<u>Column 18,</u>
Line 45, delete "ringed" and insert -- rinsed --

UNITED STATES PATENT AND TRADEMARK OFFICE
CERTIFICATE OF CORRECTION

PATENT NO.    : 6,376,516 B1
DATED         : April 23, 2002
INVENTOR(S)   : Harish C. Joshi, Keqiang Ye, Judith Kapp and Fugiang Liu It is certified that error appears in the above-identified patent and that said Letters Patent is hereby corrected as shown below:

Column 21,
Lines 15-16, delete the phrase ", with the proviso that the formula excludes noscapine of the structure"

Signed and Sealed this

First Day of October, 2002

*Attest:*

*Attesting Officer*

JAMES E. ROGAN
*Director of the United States Patent and Trademark Office*